United States Patent [19]

Eilentropp

[11] Patent Number: 5,357,948
[45] Date of Patent: Oct. 25, 1994

[54] HEATABLE RESPIRATORY HOSE

[76] Inventor: Heinz Eilentropp, Neyetal 12, D 5272 Wipperfürth, Fed. Rep. of Germany

[21] Appl. No.: 1,314

[22] Filed: Jan. 6, 1993

[30] Foreign Application Priority Data

Jan. 18, 1992 [DE] Fed. Rep. of Germany ... 9200567[U]

[51] Int. Cl.$^5$ .............................................. A61M 15/00
[52] U.S. Cl. .......................... 128/204.17; 128/203.76; 128/911
[58] Field of Search ...................... 128/204.17, 203.12, 128/203.17, 203.26, 203.27, 911

[56] References Cited

U.S. PATENT DOCUMENTS

| | | | |
|---|---|---|---|
| 3,638,926 | 2/1972 | Melville et al. | 128/203.27 |
| 4,686,354 | 8/1987 | Makin | 128/204.17 |
| 4,967,744 | 11/1990 | Chua | 128/204.17 |

FOREIGN PATENT DOCUMENTS 2173274 10/1986 United Kingdom ........... 128/204.17

OTHER PUBLICATIONS

Sax and Lewis, Sr., *Hawley's Condensed Chemical Dictionary* 11th ed, 1987, pp. 531–532 and 1039–1040.

*Primary Examiner*—Edgar S. Burr
*Assistant Examiner*—Eric P. Raciti
*Attorney, Agent, or Firm*—Ralf H. Siegemund

[57] ABSTRACT

A respiratory or respiration hose is made of a transparent or translucent material, e.g. a silicon caoutchouc, the hose has a helical, preferably hollow ridge or bar on its outer surface bonded thereto by a silicon based adhesive; heating conductors means are arranged on a foot portion of the ridge, on one or both sides of the foot portion of the ridge and are adhesively bonded to the hose; a return conductor may run through the hollow ridge interior; heating current is fed to the heating conductor which is provided in parallel or serial connection.

12 Claims, 1 Drawing Sheet

HEATABLE RESPIRATORY HOSE

BACKGROUND OF THE INVENTION

The present invention relates to a respiratory hose made of translucent or transparent rubber-elastic material having along its outer periphery a helical rib bar; also the hose is to be heated by means of an electrical conductor.

Respiration hoses of the kind to which the invention are used for example as emergency equipment to feed breathing air to a patient possibly at the site of an accident or while moving the patient to a hospital. These hoses are transparent or translucent in order to permit visual monitoring of the hose, e.g. whether or not it is plugged. The ribs or bars prevent the hose from being squeezed shut in the case of bending; i.e. these bars, etc., serve as protection.

Since the conditions of employment are often unforeseeable certain adverse weather conditions have to be taken in consideration. For instance, in a cold temperature, the outer surface of the hose may be very cold, but the hot air passing through the hose contains moisture that may readily precipitate in the hose and then be sucked in by the patient.

European Patent EP 0 214 976 31 suggests the heating of the respiration air by placing a heating wire in the inner wall of an otherwise smooth wall tube. The heating wire is loosely placed. Such a synthetic hose does not guarantee unimpeded function when bent. Moreover, the heater warms the passing air and not the hose wall. Thus, the air in the tube is cooled and precipitation and condensation of water are not avoided. In order to remedy this situation it has been suggested to insert the heating wire spirally in the hose wall. In such a case, however, the heat distribution is no longer uniform. Moreover, the arrangement of the heating wire in the spirals of the hose requires bridging the large distance to the interior of the hose. Furthermore, a considerable amount of heat is lost to the outside air owing to the fact that the spirals extend from the hose surface. The totality of heat does not contribute to the main task, namely, heating the air in the hose.

DESCRIPTION OF THE INVENTION

It is an object of the present invention to provide a new and improved respiratory or respiration hose that is independent from the weather conditions in which the hose is actually used. The hose must not pose any danger that is, for example, dependent on the climate generally and the weather in particular.

It is another object of the invention to provide such a hose that climatizes the breathing air over the entire cross-section of the hose even when moist; moreover the hose must remain in a state of operative safety throughout, i.e. independent from ambient conditions.

It is a specific object of the invention to provide a new and improved heatable, respiratory or respiration hose made of a transparent or translucent material with a helical ridge or bar.

In accordance with the preferred embodiment of the invention, the objects, particularly the specific object of the invention are attained in that the heating conductor(s) is (are) arranged directly on the outer hose surface to one or both sides of the ridge or bar and in intimate contact therewith and with the hose wall itself. The conductor(s) are connectable to an external current source to obtain heating. The ridge or bar may be solid or hollow and in the latter case the hollow space accommodates a cold return path conductor. If the ridge or bar is not integral with the hose, it is bonded thereto. Hose and ridge are preferably made of silicon caoutchouc and any bonding including the affixing of the heating conductor is carried out by a silicon based adhesive. Suitable fixtures at the hose end(s) provide for the requisite connections to the equipment and the mouthpiece.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
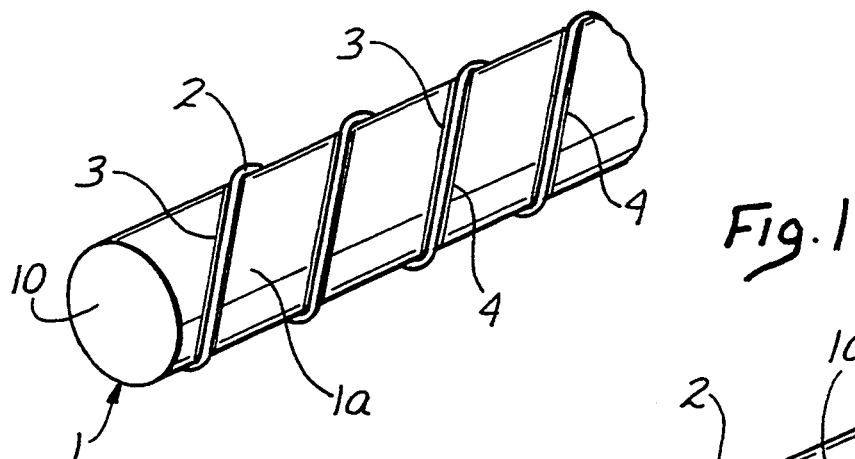
FIG. 1 is a perspective view with frontal exposed cross-section of a highly flexible hose in accordance with the preferred embodiment of the invention.
Figure 2:
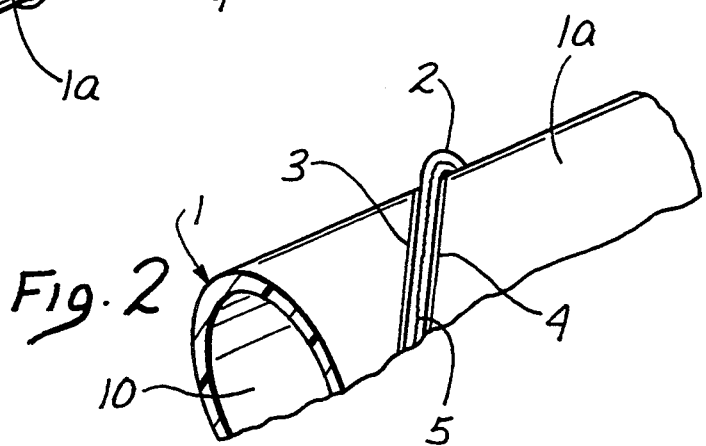
FIG. 2 shows an enlarged detail of FIG. 1.

Proceeding now to the detailed description of the drawings, FIG. 1 as well as FIG. 2 (and also FIGS. 3 and 4), illustrate a highly flexible hose 1 made, e.g. of silicon caoutchouc (rubber) that is either transparent or translucent. The outer surface 1a of the hose 1 is provided with a helical ridge or bar 2. The pitch of the helix is rather shallow as many loops are not needed. The basic function of the ridge or bar is to protect the hose against local collapse and squeezing on account of rather sharp bending that may accidentally occur. Two heating conductors 3 and 4 run along the foot portion of the ridge or bar, respectively to both sides thereof. Consequently the two conductors have also a helical configuration that run tightly on the ridge as well as the hose surface. This tight intimate and close position in relation to the ridge or bar 2 assures that the basically opaque conductors do not obliterate or otherwise obscure the view through the hose wall into the interior 10. This holds true regardless whether the heating conductors are bare or insulated, solid conductors or are twisted or braided filaments, with or without insulation. Any insulation, if provided, will be thin.

A simplified version uses but one heating conductor, e.g. 3 so that the other one, 4, does not have to be provided. This choice depends inter alia on the expected conditions of employment, e.g. if the expected heating power needed to fulfill the requisite function is high or low. Thus, where the expected ambient air may be very cold, two heating conductors will be needed. When both conductors are provided, one of them may serve as outgoing conductor and the other one for the return so that the connection is a serial one with external connection at the one end of the hose. FIG. 2 illustrates an additional feature. Here the two conductors 3 and 4 are presumed to be connected electrically in parallel and a cold conductor 5 serves as a return path. That conductor 5 runs in the interior of the ridge or bar 2. Conductor 5 may run in a hollow interior of the ridge or bar 2 but is insulated from the conductors 3 and 4 (which in this case may be but do not have to be electrically insulated). Please note that the inclusion of the return path conductor 5 inside the rib or ridge or bar 2 makes sure that the return conductor does not constitute an obscuring object as far as visibility into the interior 10 of the hose 1 is concerned.

Figure 3:
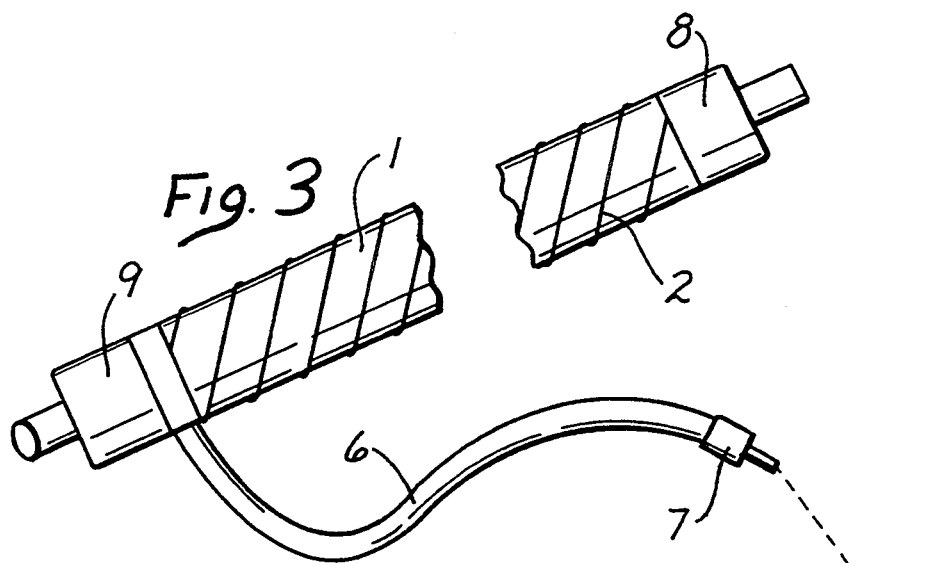
FIG. 3 is a schematic side view of such a hose.
Figure 4:
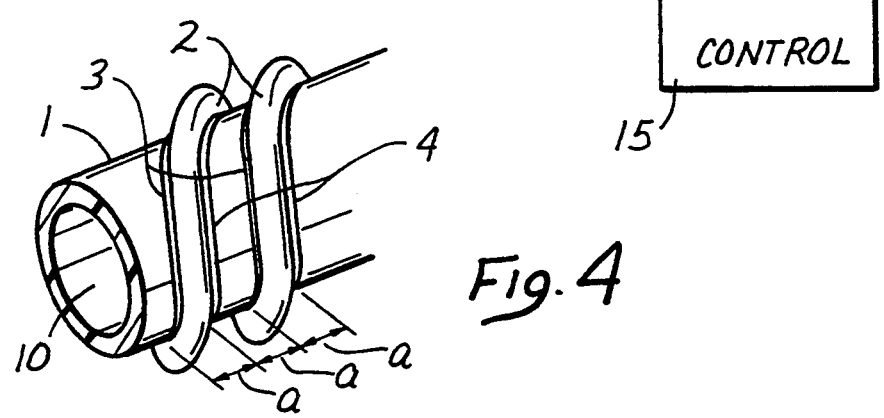
FIG. 4 is a view similar to FIG. 2 but with a more exact geometry.

FIG. 3 illustrates a standardized mass producable hose 1 for the purpose envisioned by this invention. The hose is of compact design and universally applicable. In use the hose 1 may be from 1 to 3 meters long. The standard conditions may be particularized to establish a heated hose for a temperature between about 28° C. to 38° C. Also, the air may actually be humidified to have up to 100% or just a little below relative humidity. The heating thus must be sufficient to insure that this high moisture content does not precipitate as condensation water inside tube 1.

The ridge or bar configuration 20 is as shown in FIG. 1 or 2; i.e. it is comprised of a solid or hollow ridge or bar and one or two flanking heating conductors; with or without a return path conductor 5, though the use of such a return is preferred. The structures 8 and 9 are hose connection fittings respectively for connecting the hose to a mouthpiece and to the respiratory equipment. Near end 9 is also provided the connection i.e. a cable 6 with a plug 7 for the electrical connection to an electric power supply 15. This supply will preferably include a regulator that is controllable and/or adjustable as to the heating power output provided by the device.

The inventive device thus prevents condensation of moisture in the interior wall of hose 1 in that undue cooling of the hose and therefore undue cooling of the air passing through is avoided so that condensation water will not form. Hence the air or other breathing or respiratory gas can be quite moist and yet remain so in a uniform manner. For example the moisture content may be continuously controlled at the connection end of the hose (9) through the adding and evaporating of sterilized water. In addition to the requirement of passing uniformly moist air without a liquidous water content, there is the requirement that the hose is and remains highly flexible and is also transparent or translucent for observation purposes, i.e. for observing the interior 10 of the hose 1. The reason here is that mucus or other excretions of the patient may in some form pass into the hose, a process that may interfere with the respiratory activities, necessitating for example an exchange or cleaning of the equipment.

The unobscured observation of the hose's interior is guaranteed by the fact that the heating conductors are not really in the way; i.e. the inherent but minimal obscuring of vision caused by the stiffening ridge 2 is not further augmented because the conductors 3 and 4 are right at the foot portion or root of the bar or ridge 2. This absence of additional vision obscuring holds even if in furtherance of the invention the conductors 3 and 4 are bonded to the hose, e.g. through a suitable adhesive. Since the hose is made preferably of silicon rubber, the adhesive should also be a silicon based adhesive, for directly bonding the heating conductors 3 and 4 to hose 1.

It should be observed that the entire wall of the hose need not be heated but the heating through the externally arranged conductors 3 and 4 establishes primarily a heat barrier against the ambient air and thus prevents cooling of the hose by that air. The ridge or bar 2 provides for mechanical protection of the hose to prevent it from being squeezed shut if the hose is bent rather sharply. In addition the heating conductors may be provided with an electrical insulation not only to increase voltage resistance but to enhance the mechanical strength of the heating conductors against the effects of strong hose bending. The heating conductors are thus preferably insulated by means of a fluoro-polymer. This material as well as silicon caoutchouc and silicon based adhesives readily permits hot steam sterilization of the hose as a whole following use and prior to re-use.

The ribs, ridges, or bars 2 of the hose circumscribe the hose proper as a helix. This element 2 can be solid or, as is preferred, hollow to accommodate the return path conductor 5. The ribs or ridges have as their main function the prevention of a tight shut squeeze of the hose when bent for any reason. Hence the main function of the ribs, etc., is as support for the hose as a tubular air conductor. These ribs ensure that there is always available an adequate passage way for air or other breathing gas (e.g. pure oxygen). Also, if the ridge 2 is hollow the hollowness does not diminish the support function of the hose but enhances flexibility which in turn is beneficial as far as interference through bending is concerned.

The ridge or bar 5 is basically to be understood to be of integral configuration as far as the hose is concerned. However it may be more practical to have the hose 1 and a ridge—hose manufactured separately in which case the latter must be bonded to the former. Since all these parts are to be made of silicon rubber a silicon based adhesive is also to be used here.

It was mentioned above that the helix is to be of a rather shallow pitch. This must be qualified and particularized. The axial distance a between two axially sequenced loops should be about equal to the foot width a of the ridges 2. This is shown particularly in FIG. 4. One can also say that this optimized mechanical stabilization of the hose as far as its being supported by the ridge is concerned ensures at least a 50% visibility into the hose.

The invention is not limited to the embodiments described above but all changes and modifications thereof, not constituting departures from the spirit and scope of the invention, are intended to be included.

What is claimed is:

1. Heatable respiratory or respiration hose made of a transparent or translucent material, the hose having a tubular portion with an outer surface, and a helical ridge or bar on said outer surface of the tubular portion, the ridge or bar having a foot portion with which the ridge or bar emerges radially outwardly from the surface; the improvement comprising:

heating conductor means exterior of said hose and said ridge or bar and arranged on and along said foot portion of the ridge and in intimate contact with the surface of the hose said conductor means being specifically arranged on at least one side of the foot portion and attached to the ridge or bar itself and on the surface of the hose so that the conductor means have a consistent spacing from and in relation to the hose and said surface on account of said intimate contact; and means for electrically connecting the conductor means so as to permit heating current to be fed to the heating conductor.

2. A hose as in claim 1, the heating conductor means being affixed to the hose by means of a bonding agent.

3. A hose as in claim 2, the bonding agent having a silicon base.

4. A hose as in claim 3, the hose being made of a silicon caoutchouc.

5. A hose as in claim 1, the hose being made of a silicon caoutchouc.

6. A hose as in claim 1, the heating conductor means being electrically insulated by means of an insulation.

7. A hose as in claim 6, the insulation being a fluoropolymer.

8. A hose as in claim 1, for a dual electrical connection at one end of the hose, there being an electrical return path conductor in the ridge.

9. A hose as in claim 1, the hose being a principal hose, the ridge being a separate hose bonded to the principal hose.

10. A hose as in claim 9, for a dual electrical connection at one end of the hose, there being a return conductor held in the ridge hose without being affixed thereto.

11. A hose as in claim 1, the ridge defining a helix having a pitch such that the width of the ridge is about equal to a spacing between loops of the ridge of the helix.

12. Hose as in claim 1, there being connection fittings on both ends of the hose, the means for connecting including cable connection means at one of the ends.

* * * * *